United States Patent
Sanzgiri et al.

(10) Patent No.: US 7,332,152 B2
(45) Date of Patent: Feb. 19, 2008

(54) COSMETIC COMPOSITION

(75) Inventors: Vibhav Ramrao Sanzgiri, Andheri (IN); Simone Dosu Sethna, Andheri (IN); Shivani Kiran Shah, Andheri (IN); Pushker Sona, Jatujak (TH)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 449 days.

(21) Appl. No.: 10/980,479

(22) Filed: Nov. 3, 2004

(65) Prior Publication Data

US 2005/0100517 A1    May 12, 2005

(30) Foreign Application Priority Data

Jun. 11, 2003  (IN) .................. 1165/MUM/2003
Feb. 25, 2004  (GB) .................. 0404118.2

(51) Int. Cl.
*A61K 8/36*    (2006.01)
*A61K 9/00*    (2006.01)

(52) U.S. Cl. .............. 424/62; 424/401; 514/356; 514/340; 514/552; 514/790

(58) Field of Classification Search ........... 424/401, 424/62; 514/560, 844
See application file for complete search history.

(56) References Cited

U.S. PATENT DOCUMENTS

| | | |
|---|---|---|
| 4,278,656 A | 7/1981 | Nagai et al. |
| 4,937,370 A | 6/1990 | Sabatelli |
| 4,981,681 A | 1/1991 | Tosti |
| 4,999,186 A | 3/1991 | Sabatelli et al. |
| 5,194,248 A * | 3/1993 | Holick .............. 424/59 |
| 5,262,153 A | 11/1993 | Mishima et al. |
| 5,658,580 A | 8/1997 | Mausner |
| 5,804,594 A | 9/1998 | Murad |
| 5,833,998 A | 11/1998 | Biedermann et al. |
| 6,013,279 A | 1/2000 | Klett-Loch |
| 6,019,976 A | 2/2000 | Bryant |
| 6,024,942 A * | 2/2000 | Tanner et al. .............. 424/59 |
| 6,153,177 A * | 11/2000 | Bartolone et al. ........... 424/62 |
| 2002/0168329 A1 | 11/2002 | Kini et al. |
| 2003/0198610 A1 | 10/2003 | Nakayama et al. |

FOREIGN PATENT DOCUMENTS

| | | | |
|---|---|---|---|
| DE | 1 240 224 | | 8/1962 |
| FR | 2 645 740 | | 4/1989 |
| IN | 144276 | | 2/1975 |
| IN | 169917 | | 3/1990 |
| IN | 182012 | | 10/1995 |
| JP | 60188306 A | | 9/1985 |
| JP | 63-022510 | | 1/1988 |
| JP | 04009325 A | | 1/1992 |
| JP | 7258165 A | | 10/1995 |
| JP | 2000-053529 A | * | 2/2000 |
| WO | 01/41730 A1 | | 6/2001 |
| WO | 01/70190 | | 9/2001 |
| WO | 2004/043422 | | 5/2004 |

OTHER PUBLICATIONS

Tanaka et al. "Agent for external use for skin", JP 2000-053529 A, Feb. 22, 2000, English abstract.*

* cited by examiner

*Primary Examiner*—Sreeni Padmanabhan
*Assistant Examiner*—Gina C. Yu
(74) *Attorney, Agent, or Firm*—Milton L. Honig

(57) ABSTRACT

A cosmetic composition is provided comprising vitamin $B_6$, vitamin $B_3$ and an organic acid. The components of the composition interact synergistically to enhance skin lightening.

13 Claims, No Drawings

COSMETIC COMPOSITION

BACKGROUND OF THE INVENTION

1. Field of the Invention

The present invention relates to a synergistic skin lightening composition. The invention particularly relates to a composition with a combination of skin lightening actives suitable for obtaining improved skin lightening.

2. The Related Art

Melanin is the black pigment of hair and skin and is synthesized from the amino acid tyrosine by melanosomes. Melanosomes are organelles found in melanocytes, a cell type present at the dermis-epidermis junction. Tyrosine is acted upon by an enzyme, tyrosinase, which is the key step in melanogenesis. There have been several reports wherein inhibitors of tyrosinase such as hydroquinone and its derivatives, kojic acid, catechols, mercaptoamines, alpha hydroxy acids and others have been used in cosmetic compositions to regulate skin pigmentation.

IN182012 (Hindustan Lever Ltd., 1994), discloses synergistic compositions suitable for topical application to the human skin comprising dicarboxylic acids in combination with ascorbic acid in cosmetically compatible carriers. They also mention that additionally other whitening agents such as niacinamide and/or sunscreens (inorganic and/or organic) may also be present.

Use of alpha-hydroxy acids in cosmetic compounds for imparting various skin benefits such as improving the texture of the skin, increasing smoothness, firmness, moisture content is reported in U.S. Pat. No. 5,658,580 (Chanel, Inc., 1997). U.S. Pat. No. 5,262,153 (Kabushiki, 1993), discloses lactic acid and its derivatives as useful skin whitening agents which act by suppressing melanogenesis by inhibiting formation of tyrosinase.

In the melanosomes melanin is synthesised (polymerized) from monomers and is transferred to the neighbouring keratinocytes. The keratinocytes divide and differentiate and thus transport the melanosome to the surface of the skin. The intensity of the skin colour is directly related to the number, the size, the melanin content, dispersion of melanin, the rate of formation and migration/transfer of melanosomes to the keratinocytes.

Other approaches have been to use niacin/niacinamide or other skin lightening agents which are believed to control dispersion of melanosomes or inhibit tyrosinase.

IN 144276 (Hindustan Lever Ltd., 1975), discloses the combination of niacinamide and a suitable mixture of UV absorbers which absorb in the UV range of 290 nm to 360 nm. IN169917 (Hindustan Lever Ltd., 1989), discloses the use of silicone compound to synergistically enhance the skin lightening benefit obtained from the combination of niacinamide and sunscreens.

The sunscreens that are commonly used in skin lightening compositions maintain skin colour by preventing darkening of the skin due to ultra violet (UV) light. The sunscreens are materials, which absorb incident ultra violet light of the wavelength which produces the tanning and darkening of the skin.

Vitamin B6, also called pyridoxine, is closely related to water-soluble substances such as pyridoxine hydrochloride, pyridoxal, and pyridoxamine, in form and function. Pyridoxine supplementation is used for a variety of skin problems including dandruff, eczema, dermatitis, and psoriasis. It is the active component for a number of anti-aging formulations. JP04009325 (Sunstar Inc., 1992), disclose a beautifying and whitening cosmetic obtained by blending mycelial culture of Ganoderma lucidum Karst. and/or an extract essence thereof with one or more selected from ascorbic acid, retinol, pyridoxine, pantothenic acid, tocopherol, salts and derivatives thereof as an active ingredient. JP60188306 (Shiseido, 1985), discloses a cosmetic composition comprising pyridoxine or a derivative in combination with ascorbic acid for significantly improving the skin whitening effect.

U.S. Pat. No. 5,833,998 (P&G, 1998), discloses topical compositions for regulating the oily and/or shiny appearance of skin comprising an active selected from one or more compounds from the group consisting of niacinamide, pyridoxine, panthenol, and pantothenic acid, in a cosmetically acceptable carrier for said active.

However, none of the prior art teaches a synergistic cosmetic composition comprising vitamin B3, vitamin B6 and anyone of mono-, di- or poly- carboxylic or phenolic acids to obtain improved lightening or reduction of pigmentation of the skin.

It is an object of the present invention to provide a synergistic cosmetic composition comprising vitamin B6, vitamin B3 and any one of mono, di or poly carboxylic or phenolic acids that can lighten the skin significantly.

It is another object of the present invention to provide a synergistic cosmetic composition comprising vitamin B6, vitamin B3 and any one of mono, di or poly carboxylic or phenolic acids useful both for normal skin as well as skin damaged by UVR.

The compositions are also useful in treating freckles, hyper-pigmented skin, blotchy skin, melasmas, cholasmas, age spots, dark circles, etc.

SUMMARY OF THE INVENTION

According to the first aspect of the invention, there is provided a synergistic skin lightening composition comprising:

i. 0.05-10% by weight vitamin B6 or derivative thereof;
ii. 0.05-10% by weight vitamin B3 or derivative thereof; and
iii. 0.05-20% by weight at least one organic acid selected from the group consisting of $C_1$-$C_{16}$ monocarboxylic acids, dicarboxylic acids, polycarboxylic acids, phenolic acids, and esters/salts or other derivatives thereof.

According to a preferred aspect of the invention, there is provided a synergistic skin lightening composition comprising i. 0.05-10% by weight vitamin B6 or derivative thereof;
ii. 0.05-10% by weight vitamin B3 or derivative thereof;
iii. 0.05-20% by weight at least one organic acid selected from the group consisting of $C_1$-$C_{16}$ monocarboxylic acids, dicarboxylic acids, polycarboxylic acids, phenolic acids, and esters/salts or other derivatives thereof; and
iv. 0.1 to 10% weight of at least one sunscreen; and/or
v. a cosmetically acceptable vehicle and/or 10-85% detergent active.

It is particularly preferred that the cosmetically acceptable vehicle comprises 0.1 to 25% by weight of the composition of solid asymmetric particles and an anionic emulsifier, wherein the pH of the composition is between 3 and 11 and preferably between 3 and 8 and even more preferably between 3.5 and 6.

DETAILED DESCRIPTION OF THE INVENTION

According to the essential aspects of the present invention a combination of vitamin B6, vitamin B3 and at least mono, di or poly carboxylic or phenolic acids/esters/salts or derivatives thereof gives enhanced skin lightening benefits.

The composition according to the invention may be formulated as leave-on, or rinse-off products. The topical leave-on compositions useful in the present invention may be made into a wide variety of product formats. These include, but are not limited to, lotions, creams, gels, sticks, sprays, wipes, face packs, ointments, pastes, mousses and cosmetics (e.g., solid, semi-solid, liquid make-up, including foundations). These product types may comprise several types of carriers including, but not limited to solutions, aerosols, emulsions (including water-in-oil and oil-in-water), gels, solids, and liposomes. They may be in the form of rinse-off products like soap bars, detergent powders, flakes, liquids, gels, etc. The composition of the present invention may also be formulated as talcum powder, liquid talc or compact.

Skin Lightening Vitamins

It is an essential feature of the invention that Vitamin B6 or its derivative thereof be present in combination with vitamin B3 or its derivatives in the skin lightening composition of the invention. Vitamin B6, as defined herein, refers to a family of water-soluble substances that include pyridoxine hydrochloride, pyridoxal, and pyridoxamine, which are closely related in form and function. Vitamin B6 is available as synthetic material and is also found naturally in animal foods and plants. Liver, salmon, fish, chicken, ham, eggs, pork, beef, split peas, dried beans, banana, avocado, watermelon, turnip greens, brussel sprouts, potato, sweet potato, carrots, peas, chickpeas, brewer's yeast, wheat bran, wheat germ, kidney, heart, cantaloupe, cabbage, blackstrap molasses, and milk are some important sources of vitamin B6. It is thus possible to choose B6 available from any known source that may be natural or synthetic or any commercially available source.

Another essential ingredient of the composition is niacinamide or nicotinamide which form the biologically active form of vitamin B3. Exemplary derivatives of vitamin B3 compounds include nicotinic acid esters, including non-vasodilating esters of nicotinic acid, nicotinyl amino acids, nicotinyl alcohol esters of carboxylic acids, nicotinic acid N-oxide and niacinamide N-oxide.

Vitamin B6 is incorporated at 0.05-10% by weight of the composition and is preferably present in an amount from 0.1 to 5%, more preferably 0.5-2% by weight of the cosmetic composition. Vitamin B3 is incorporated at 0.05-10% by weight of the composition and is preferably present in an amount from 0.1 to 5%, more preferably 0.5-2% by weight of the cosmetic composition.

Other skin lightening vitamins can be advantageously included in the composition to provide for synergistic skin lightening effects. These include vitamin B12, vitamin C, vitamin E, vitamin A, vitamin D, vitamin K, or their precursors/salts/esters/derivatives. Mixtures of the vitamins can also be employed in the composition of the invention. Especially preferred vitamins are vitamin B12, vitamin E and vitamin C.

Organic Acids

The organic acids may be chosen from mono, di, poly carboxylic or phenolic acids or their salts, esters or derivatives thereof.

Monocarboxylic acids may be either substituted or unsubstituted. The monocarboxylic acids have a carbon chain length of up to 16 (i.e. $C_1$-$C_{16}$ acids), more preferably up to 14 (i.e. $C_1$-$C_{14}$ acids) and most preferably up to 12 (i.e. $C_1$-$C_{12}$ acids). Particularly preferred monocarboxylic acids are ascorbic acid or α-, β- or poly-hydroxy acids that include glycolic acid, lactic acid, 2-hydroxy-octanoic acid, salicylic acid, and/or mixtures thereof. The particularly preferred β-hydroxy carboxylic acid is lactic acid or a salt thereof such as ammonium lactate. The particularly preferred β-hydroxy carboxylic acid is salicylic acid.

Dicarboxylic acids suitable for the present invention are represented by the formula HOOC—$(C_xH_y)$—COOH where $C_xH_y$ is optionally substituted and x=0 to 20 and y=0 to 40. Particularly preferred dicarboxylic acids include azelaic acid, sebacic acid, oxalic acid, succinic acid, fumaric acid. Polycarboxylic acids include but are not limited to citric acid.

The organic acid may also be a vitamin acid including ascorbic acid, retinoic acid or pantethenoic acid. Organic acids also include natural acids such as glycertenic acid and polyglyceric acid. Acids of reducing and non-reducing sugars may also be used as an organic acid.

Particularly preferred phenolic acids are selected from ferulic acid, salicylic acid, kojic acid.

Preferably the organic acids of this invention are water-soluble. By "water-soluble" is meant that the acid has an aqueous solubility of at least 0.1 g per 100 g of water at 20° C.

Skin Lightening Agents

Other known skin lightening agents such as hydroquinone and derivatives (e.g. arbutin, 4-hydroxyanisol, mequinol, HMBE, monobenzone, etc.), retinol and its derivatives (e.g. Tretinoin, retinoic acid), resorcinol and its derivatives (e.g 4-alkyl resorcinols, etc.), reservatol, ellagic acid, linoleic acid and α-lipoic acid, natural skin lightening extracts and mixtures thereof may be incorporated.

Sunscreens

The composition of the invention preferably includes an effective amount of a sunscreen and/or sun-block agent to enhance synergistically the benefit of the composition in providing for skin lightening. Organic and inorganic sunscreens/sun-blocks or combinations thereof may be suitably employed in the composition.

Ultraviolet light is a predominant cause of skin darkening. Thus, for purposes of skin lightening, compositions comprising UVA and/or UVB sunscreen are desirable.

A wide variety of conventional sunscreen agents are suitable for use in combination with the skin lightening composition of the present invention. Suitable sunscreen agents include, p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, a-phenyl cinnamonitrile; butyl cinnamoyl pyruvate); dihydroxycinnamic acid derivatives (umbelliferone, methylumbelliferone, methylaceto-umbelliferone); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naphthol-sulfonates (sodium salts of 2-naphthol-3,6-disulfonic and of 2-naphthol-6,8-disulfonic acids); di-hydroxy-naphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives (e.g., hexaethylether); (butyl carbotol) (6-propyl piperonyl) ether; hydroquinone; benzophenones (oxy-benzene, sulisobenzone, dioxybenzone, benzoresorcinol, 2,2',4,4'-tetrahydroxybenzophenone, 2,2'-dihydroxy-4, 4'-dimethylbenzophenone, octabenzone); 4-isopropyldibenzoylmethane; butyl-methoxydibenzoylmethane; etocrylene; and 4-isopropyl-di-benzoylmethane.

Of these, 2-ethylhexyl-p-methoxycinnamate, 4,4'-t-butylmethoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4-(bis(hydroxypropyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid and mixtures of these compounds, are preferred.

More preferred sunscreens useful in the compositions useful in the subject invention are 2-ethylhexyl-p-methoxycinnamate, butylmethoxydibenzoylmethane, 2-hydroxy-4-methoxybenzophenone, octyldimethyl-p-aminobenzoic acid and mixtures thereof.

Also particularly useful in the compositions are sunscreens such as those disclosed in U.S. Pat. No. 4,937,370 issued to Sabatelli on Jun. 26, 1990, and U.S. Pat. No. 4,999,186 issued to Sabatelli & Spirnak on Mar. 12, 1991, both of which are incorporated herein by reference. The sunscreen agents disclosed therein have, in a single molecule, two distinct chromophore moieties, which exhibit different ultra-violet radiation absorption spectra. One of the chromophore moieties absorbs predominantly in the UVB radiation range and the other absorbs strongly in the UVA radiation range.

A safe and effective amount of sunscreen may be used in the compositions useful in the subject invention. The composition preferably comprises from about 0.1% to about 10%, more preferably from about 0.1% to about 5%, of one or more sunscreen agent(s).

Useful inorganic sunscreens or sun-blocks include, but are not limited to, zinc oxide iron oxide, silica, such as fumed silica, and titanium dioxide.

Ultrafine titanium dioxide in either of its two forms, namely water-dispersible titanium dioxide and oil-dispersible titanium dioxide is especially suitable for the invention.

Water-dispersible titanium dioxide is ultra-fine titanium dioxide, the particles of which are non-coated or which are coated with a material to impart a hydrophilic surface property to the particles. Examples of such materials include aluminium oxide and aluminium silicate.

Oil-dispersible titanium dioxide is ultrafine titanium dioxide, the particles of which exhibit a hydrophobic surface property, and which, for this purpose, can be coated with metal soaps such as aluminium stearate, aluminium laurate or zinc stearate, or with organosilicone compounds.

By topical application to the skin of a mixture of inorganic sunscreens or sunblock agents and/or organic sunscreens, synergistically enhanced protection of the skin against the harmful effects of both UV-A and UV-B rays is achievable.

The total amount of inorganic sunscreen or sun block that is preferably incorporated in the composition according to the invention is from 0.1 to 5% by weight of the composition.

Cosmetically Acceptable Vehicle

The composition according to the invention also comprises a cosmetically acceptable vehicle to act as a diluent, dispersant or carrier for other materials present in the composition, so as to facilitate their distribution when the composition is applied to the skin.

The phrase "cosmetically acceptable vehicle", as used herein, means one or more compatible solid or liquid fillers, diluents, extenders and the like, which are cosmetically acceptable as defined herein. The term "compatible", as used herein, means that the components of the compositions of this invention are capable of being comingled with the primary actives of the present invention, and with each other, in a manner such that there is no interaction which would substantially reduce the efficacy of the composition under ordinary use situations. The type of carrier utilized in the present invention depends on the type of product desired.

Vehicles other than water can include liquid or solid emollients, oils, silicone oils, solvents, humectants, thickeners, emulsifiers, propellants and powders. Each of these types of vehicle can be used singly or in mixtures of one or more vehicles,. Such mixtures may be in the form of emulsions (O/W, W/O or W/O/W).

Emollients and oils, include but are not limited to stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rapeseed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate; etc.

Non-limiting examples of silicone oils include polydimethylsiloxanes, cyclomethicones, phenyltrimethicone, dimethiconol and mixtures thereof.

Water is a preferred solvent. Examples of suitable organic solvents include: propylene glycol, polyethylene glycol, polypropylene glycol, glycerol, 1,2,4-butanetriol, 1,2,6-hexanetriol, ethanol, isopropanol, sorbitol esters, butanediol, acetone, ethylene glycol monoethyl ether, diethylene glycol monobutyl ether, diethylene glycol monoethyl ether and mixtures thereof.

Humectants can be selected from glycerin, diglycerin, triglycerin, polyglycerin, ethoxylated and propoxylated glycerols polypropylene glycol, polyethylene glycol, ethylene glycol, diethylene glycol, triethylene glycol, propylene glycol, dipropylene glycol, hexylene glycol, 1,3-butylene glycol, 1,4-butylene glycol. Among the polyhydric alcohols, propylene glycol and dipropylene glycol are preferred.

Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate can be selected.

Examples of suitable thickeners include polymeric thickeners such as acrylates/C10-30 alkyl acrylate crosspolymers, polyacrylamides, cationic polymers, gums (e.g., xanthan gum, guar gum), and cellulose derivatives (e.g., hydroxyethyl cellulose, hydroxy propyl cellulose).

Propellants, include but are not limited to propane, butane, isobutane, dimethyl ether, carbon dioxide and nitrous oxide.

In forming mixtures of vehicles or emulsions, selected anionic and/or nonionic emulsifiers may also be optionally, but preferably included.

Suitable anionic emulsifiers may be selected from among alkyl sulphates, aralkyl sulphates, alkyl ethoxy ether sulphates, alkaryl sulphonates, alkyl succinates, alkyl sulphosuccinates, N-alkoyl sarcosinates, isethionates, N-acyl taurate, fatty acid amides of methyl tauride and combinations thereof. For example, salts of sulfuric acid monoesters or phosphoric acid monoesters, salts of $C_{12-18}$ fatty acids, of $C_{12-18}$ fatty alcohols, of $C_{12-18}$ acyl isethionic acids, of $C_{12-18}$ alkane sulfonic acids or of $C_{12-18}$ acylamino acids may be selected. Non-limiting examples of anionic surfactants include phosphate esters such as sodium polyoxyethylene (10) lauryl ether phosphate, DEA cetyl phosphate, potassium cetyl phosphate, phosphorous organic derivatives such as phosphated oleyl ether (10 ethylene oxide), sodium lauryl sulphate and sodium cetostearyl sulphate.

Non-limiting examples of suitable nonionic emulsifiers are fatty alcohols, fatty acid monoglycerides, glyceryl monostearate and diglyceryl monostearate, ethoxylated and propoxylated fatty acids such as polyoxyethylene (100)-stearate propylene glycol monostearate, sorbitan fatty acid esters such as sorbitan monostearate, polyoxyethylene (20) sorbitan monostearate, ethoxylated fatty alcohols like polyoxyethylene (21) stearyl ether, polyoxyethylene (2) stearyl ether, polyoxyerthylene (10) hydrogenated castor oil, fatty acid alkanolamides such as coconut diethanolamide and lauramide DEA, block polymers such as block copolymer of propylene oxide and ethylene oxide, alkyl polyglucosides, sucrose and glucose esters and derivatives such as saccharose distearate and sucrose stearate and polyglycerol fatty acid esters. Other nonionic emulsifiers include ethoxylated alkylphenols such as polyoxyethylene (10) nonylphenyl ether, ethoxylated fatty acids such as polyethyleneglycol (10 ethylene oxide) monostearate, ethoxylated fatty esters such as polyoxyethylene (5) glyceryl monostearate, ethoxylated fatty esters and oils such as glycerol esters such as lanolin-based derivatives such as polyoxyethylene lanolin, propoxylated and ethoxylated fatty acids, alcohols or alkyl phenols such as polyoxyethylene (10) polyoxypropylene (4) cetyl ether, and protein-based surfactants such as polyoxyethylene (25) glycerin monopyoglutamic monoisostearate. The nonionic emulsifiers preferably include the following either alone or in combination: ethoxylated alkyl ethers (under the trade name Brij); sorbitan esters (under the trade name Span); ethoxylated sorbitan esters (under the trade name Tween); ethoxylated fatty acid esters (under the trade name Myrj); fatty alcohols; ethoxylated fatty alcohols of glycerin; and fatty acids.

Suitable solid asymmetric particles include fatty acid crystals, mica, talc, clays and mixtures thereof. The preferred solid particles are selected from fatty acid crystals wherein the fatty acid contains from 12-22 carbon atoms, because they are inexpensive and the most aesthetically acceptable. The most preferred fatty acid is stearic acid. The exact amount depends on the final composition and the nature of the other ingredients in the composition.

Detergent Active

It is also possible to provide the skin lightening composition of the invention in the form of a wash off product for personal cleansing. A detergent active is a preferred component of such compositions and may be selected from either soap or non-soap actives. The detergent actives may be selected from anionic, nonionic, cationic, amphoteric or zwitterionic actives. Such actives are disclosed in standard detergent textbooks for example "Surface Active Agents", Volume I by Schwartz and Perry and "Surface Active Agents and Detergents", Volume II by Schwartz, Perry and Berch.

The term soap denotes salts of carboxylic fatty acids. The soap may be derived from any of the triglycerides conventionally used in soap manufacture—consequently the carboxylate anions in the soap may contain from 8 to 22 carbon atoms.

For soap having 18 carbon atoms, an accompanying sodium cation will generally amount to about 8% by weight. Other cations may be employed as desired for example zinc, potassium, magnesium, alkyl ammonium and aluminium.

The soap may be obtained by saponifying a fat and/or a fatty acid. The fats or oils generally used in soap manufacture may be such as tallow, tallow stearines, palm oil, palm stearines, soya bean oil, fish oil, caster oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soya bean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources and generally comprise about 1-8% myristic acid, about 21-32% palmitic acid, about 14-31% stearic acid, about 0-4% palmitoleic acid, about 36-50% oleic acid and about 0-5% linoleic acid. A typical distribution is 2.5% myristic acid, 29% palmitic acid, 23% stearic acid, 2% palmitoleic acid, 41.5% oleic acid, and 3% linoleic acid. Other similar mixtures, such as those from palm oil and those derived from various animal tallow and lard are also included.

Coconut oil refers to fatty acid mixtures having an approximate carbon chain length distribution of 8% $C_8$, 7% $C_{10}$, 48% $C_{12}$, 17% $C_{14}$, 8% $C_{16}$, 2% $C_{18}$, 7% oleic and 2% linoleic acids (the first six fatty acids listed being saturated). Other sources having similar carbon chain length distributions, such as palm kernel oil and babassu kernel oil, are included within the term coconut oil.

Optional Cosmetic Ingredients

The compositions of the present invention can comprise a wide range of other optional components. The OTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants; binders; biological additives; buffering agents; colorants; thickeners; polymers; astringents; fragrance; humectants; opacifyi ng agents; pH adjusters; preservatives; natural extracts; essential oils; skin sensates; skin soothing agents; and skin healing agents.

The invention is now further described by way of the following non-limiting examples.

EXAMPLE 1

Seven comparative formulations (F1 to F7) and a formulation according to the invention (F8) were prepared by mixing the components as listed in Table 1.

The various formulations described were used to test their efficacy for skin lightening benefits using a panel of 30 volunteers with uniform skin colour. The initial skin colour was recorded. The formulation was applied on their volar forearms by trained applicators at pre-designated sites. The formulation was applied 5 times a day on each site with a gap of 2 hours between each application, with the forearm being washed only before the first application of the day and after the last application of the day. At the end of 40 applications the change in colour was recorded. Visual grading was used for quantifying the change in colour by directed difference to the area surrounding the area to which the formulation was applied. The differences between the base alone (placebo) and the treatment sites were indicative of the efficacy of the formulation and a negative skin lightening value indicates lightening and positive value indicates darkening.

TABLE 1

| | % composition by weight | | | | | | | |
|---|---|---|---|---|---|---|---|---|
| Ingredients | F1 | F2 | F3 | F4 | F5 | F6 | F7 | F8 |
| Stearic acid | 18.00 | 18.00 | 18.00 | 18.00 | 18.00 | 18.00 | 18.00 | 18.00 |
| Cetyl alcohol | 0.40 | 0.40 | 0.40 | 0.40 | 0.40 | 0.40 | 0.40 | 0.40 |
| Glyceryl monostearate | 0.60 | 0.60 | 0.60 | 0.60 | 0.60 | 0.60 | 0.60 | 0.60 |
| Silicone oil | 0.50 | 0.50 | 0.50 | 0.50 | 0.50 | 0.50 | 0.50 | 0.50 |
| Sodium cetostearyl sulphate | 1.0 | 1.0 | 1.0 | 1.0 | 1.0 | 1.0 | 1.0 | 1.0 |
| Mixture of sorbitan esters and ethoxylated fatty acid esters) | 1.5 | 1.5 | 1.5 | 1.5 | 1.5 | 1.5 | 1.5 | 1.5 |
| Alkyl acrylate cross polymer | 0.15 | 0.15 | 0.15 | 0.15 | 0.15 | 0.15 | 0.15 | 0.15 |
| Polyhydric alcohol | 10.00 | 10.00 | 10.00 | 10.00 | 10.00 | 10.00 | 10.00 | 10.00 |
| Preservatives | 0.5 | 0.5 | 0.5 | 0.5 | 0.5 | 0.5 | 0.5 | 0.5 |
| EDTA | 0.04 | 0.04 | 0.04 | 0.04 | 0.04 | 0.04 | 0.04 | 0.04 |
| Vitamin B3 | — | 1.00 | — | — | 1.00 | 1.00 | — | 1.00 |
| Vitamin B6 | — | — | 1.00 | — | 1.00 | — | 1.00 | 1.00 |
| Sebacic acid | — | — | — | 0.75 | — | 0.75 | 0.75 | 0.75 |
| Water | | | | To 100 | | | | |

The data presented in table 2 below shows the average skin lightening score calculated as an average over all volunteers of the directed difference scores.

TABLE 2

| | F1 | F2 | F3 | F4 | F5 | F6 | F7 | F8 |
|---|---|---|---|---|---|---|---|---|
| Skin lightening efficacy | 0.0 | −0.09 | −0.03 | −0.12 | −0.02 | −0.16 | −0.11 | −0.28 |

The data presented in table 2 show that only a combination of vitamin B3, and vitamin B6 with a carboxylic acid (F8) gives a synergistic skin lightening benefit. With either vitamin alone along with the carboxylic acid (F6 or F7) or a combination of the two vitamins (F5) there is no significant improvement over the individual actives alone (F2, F3 or F4).

EXAMPLE 2

Three comparative formulations (F9 to F11) and a formulation according to the invention (F12) were prepared by mixing the components as listed in Table 3.

The efficacy of the formulations for skin lightening was tested using a panel of 30 volunteers with uniform skin color. The initial skin color was recorded. The formulation was applied on their volar forearms by trained applicators at pre-designated sites. The formulation was applied 5 times a day on each site with a gap of 2 hours between each application, with the forearm being washed only before the first application of the day and after the last application of the day. At the end of 25 applications the change in color was recorded. Visual grading was used for quantifying the change in colour by directed difference to the area surrounding the area to which the formulation was applied. The differences between the base alone (placebo) and the treatment sites were indicative of the efficacy of the formulation and a negative skin lightening value indicates lightening and positive value indicates darkening.

TABLE 3

| | % composition by weight | | | |
|---|---|---|---|---|
| Ingredients | F9 | F10 | F11 | F12 |
| Stearic acid | 18.00 | 18.00 | 18.00 | 18.00 |
| Cetyl alcohol | 0.40 | 0.40 | 0.40 | 0.40 |
| Glyceryl monostearate | 0.60 | 0.60 | 0.60 | 0.60 |
| Silicone oil | 0.50 | 0.50 | 0.50 | 0.50 |
| Sodium cetostearyl sulphate | 1.0 | 1.0 | 1.0 | 1.0 |
| Mixture of sorbitan esters and ethoxylated fatty acid esters) | 1.5 | 1.5 | 1.5 | 1.5 |
| Alkyl acrylate cross polymer | 0.15 | 0.15 | 0.15 | 0.15 |
| Polyhydric alcohol | 10.00 | 10.00 | 10.00 | 10.00 |
| Preservatives | 0.5 | 0.5 | 0.5 | 0.5 |
| EDTA | 0.04 | 0.04 | 0.04 | 0.04 |
| Vitamin B3 | — | 1.00 | — | 1.00 |
| Vitamin B6 | — | — | 1.00 | 1.00 |
| Ferulic acid | — | 1.00 | 1.00 | 1.00 |
| Water | | to 100 | | |

The data presented in table 4 below shows the average skin lightening score calculated as an average over all volunteers of the directed difference scores.

TABLE 4

| | F9 | F10 | F11 | F12 |
|---|---|---|---|---|
| Skin lightening efficacy | 0.0 | −0.03 | −0.04 | −0.11 |

The data presented in Table 4 show that a combination of vitamin B3, and vitamin B6 with another acidic active (ferulic acid) gives synergistic skin lightening benefit not seen with either vitamin alone in combination with the acid.

Thus it has been possible by the present invention to provide a synergistic skin lightening composition comprising the combination of the vitamins B3 and B6 along with carboxylic acids.

The invention claimed is:

1. A skin lightening cosmetic composition comprising:
   i. 0.05-10% by weight vitamin $B_6$ or derivative thereof;
   ii. 0.05-10% by weight vitamin $B_3$ or derivative thereof; and
   iii. 0.05-20% by weight of sebacic acid and esters/salts thereof.

2. The composition as claimed in claim 1 additionally comprising from 0.1 to 10% by weight of at least one sunscreen.

3. The composition as claimed in claim 2 wherein the sunscreen is organic or inorganic or a combination thereof.

4. The composition as claimed in claim 1 additionally comprising from 10 to 85% by weight of a detergent active.

5. The composition as claimed in claim 4 wherein the detergent active is selected from the group consisting of an anionic active, a nonionic active, a cationic active, an amphoteric active, a zwitterionic active, and mixtures thereof.

6. The composition as claimed in claim 1 additionally comprising a cosmetically acceptable vehicle.

7. The composition as claimed in claim 6 wherein the cosmetically acceptable vehicle comprises from 0.1 to 25% by weight of the composition of solid asymmetric particles and an anionic emulsifier.

8. The composition as claimed in claim 1 wherein the pH of the composition is between 3 and 11.

9. The composition as claimed in claim 1 wherein the vitamin $B_6$ or derivative thereof is selected from a synthetic or natural source.

10. The composition as claimed in claim 1 wherein the vitamin $B_3$ or derivative thereof is selected from the group consisting of niacinamide, nicotinamide, nicotinic acid esters, non-vasodilating esters of nicotinic acid, nicotinyl amino acids, nicotinyl alcohol esters of carboxylic acids, nicotinic acid N-oxide, niacinamide N-oxide, and mixtures thereof.

11. The composition as claimed in claim 1 wherein the vitamin $B_6$ or derivative thereof is incorporated at 0.1 to 5% by weight of the composition.

12. The composition as claimed in claim 1 wherein the vitamin $B_3$ or derivative thereof is incorporated at 0.1 to 5% by weight of the composition.

13. A skin lightening cosmetic composition comprising:
   i. 0.05-10% by weight vitamin $B_6$ or derivative thereof;
   ii. 0.05-10% by weight vitamin $B_3$ or derivative thereof; and
   iii. 0.05-20% by weight of ferulic acid and esters/salts thereof.

* * * * *